United States Patent
Del Soldato et al.

(10) Patent No.: US 7,199,141 B2
(45) Date of Patent: Apr. 3, 2007

(54) DRUGS FOR CHRONIC PAINS

(75) Inventors: Piero Del Soldato, Monza (IT); Ennio Ongini, Segrate (IT)

(73) Assignee: Nicox S.A., Sophia Antipolis (FR)

( * ) Notice: Subject to any disclaimer, the term of this patent is extended or adjusted under 35 U.S.C. 154(b) by 312 days.

(21) Appl. No.: 10/480,805

(22) PCT Filed: May 10, 2002

(86) PCT No.: PCT/EP02/05166

§ 371 (c)(1),
(2), (4) Date: Dec. 19, 2003

(87) PCT Pub. No.: WO03/000642

PCT Pub. Date: Jan. 3, 2003

(65) Prior Publication Data

US 2004/0171682 A1 Sep. 2, 2004

(30) Foreign Application Priority Data

Jun. 21, 2001 (IT) .......................... MI2001A1308

(51) Int. Cl.
*A61K 31/44* (2006.01)
*C07C 229/00* (2006.01)

(52) U.S. Cl. .................. 514/357; 514/506; 546/335; 560/19; 560/125; 560/128; 560/16; 560/147; 564/241

(58) Field of Classification Search ................ 560/19, 560/125, 128, 16, 147; 504/241; 546/335; 514/357, 506, 513, 634
See application file for complete search history.

(56) References Cited

U.S. PATENT DOCUMENTS 5,844,696 A * 12/1998 Masia et al. ................ 558/482
6,187,338 B1 * 2/2001 Caruso et al. ............... 424/468

FOREIGN PATENT DOCUMENTS

| WO | 95/09831 | 4/1995 |
|---|---|---|
| WO | WO 95 30641 A | 11/1995 |
| WO | WO 96 19233 A | 6/1996 |
| WO | 97/16405 | 5/1997 |
| WO | WO 98 09948 A | 3/1998 |
| WO | WO 00 06567 A | 2/2000 |
| WO | WO 00 44705 A | 8/2000 |
| WO | WO 00 54773 A | 9/2000 |
| WO | WO 00 66582 A | 11/2000 |
| WO | 00/76958 | 12/2000 |
| WO | 01/12584 | 2/2001 |
| WO | WO 01 83490 A | 11/2001 |
| WO | WO 02 30866 A | 4/2002 |
| WO | WO 02 30867 A | 4/2002 |

OTHER PUBLICATIONS

Radomski et al., "The anti-aggregating properties of vascular endothelium: interactions between prostacyclin and nitric oxide", BR. J. Pharmac. (1987), 92, pp. 639-646.
Bennett et al., "A peripheral mononeuropathy in rat that produces disorders of pain sensation like those seen in man", Pain, 33 (1988), pp. 87-107.
Xu et al., "Chronic pain-related syndrome in rats after ischemic spinal cord lesion: a possible animal model for pain in patients with spinal cord injury" Pain, 48 (1992), pp. 279-290.
Hao et al., "Treatment of a chronic allodynia-like response in spinally injured rats: effects of systemically administered excitatory amino acid receptor antagonists", Pain, 66, (1996), pp. 279-285.
Martindale, The Extra Pharmacopoeia 13 th Edition, p. 374.

* cited by examiner

*Primary Examiner*—Joseph K. McKane
*Assistant Examiner*—Robert Shiao
(74) *Attorney, Agent, or Firm*—Arent Fox LLP

(57) ABSTRACT

Nitro-oxyderivative compounds or salts thereof having the following general formula (I): $A-(B)_{b0}-(C)_{c0}-NO_2$ wherein: c0 is an integer and is 0 or 1, b0 is an integer and is 0 or 1, $A=R-T_1-$, wherein R is the radical of an analgesic drug for the chronic pain, in particular for the neuropathic pain; B is such that its precursor is selected from anminoacids, hydroxyacids, polyalcohols, compounds containing at least one acid function; C is a bivalent radical containing an aliphatic, heterocyclic or aromatic radical.

9 Claims, No Drawings

DRUGS FOR CHRONIC PAINS

CROSS-REFERENCE TO RELATED APPLICATION

This application is a National Stage entry of International Application No. PCT/EP 02/05166, filed May 10, 2002, the entire specification claims and drawings of which are incorporated herewith by reference.

The present invention relates to compounds having an improved efficacy in the reduction of the chronic pain, specifically the neuropathic pain.

For the description of the chronic pain, for simplicity, reference is made, from now on, to the neuropathic pain.

It is known that the neuropathic pain is a form of chronic pain originated from a damage or from a disease of the central or peripheral nervous system. The neuropathic pain comprises a series of painful symptomatologies, such for example the following: the diabetic neuropathic pain, the painful post-infarct syndrome, the pain caused by the chemotherapeutic treatment, or it can derive from an infection caused by viral agents, such for example herpes, for instance Herpes zoster, etc.

The neuropathic pain generally afflicts the patients for years since the therapies with conventional analgesic drugs are not effective. Furthermore it is a social problem since the neuropathic pain besides the physical trouble causes in the patients a serious psychological stress.

In the last twenty years the research on the pathogenesis of the neuropathic pain has achieved significant progress. Studies carried out on human and animal experimental models of neuropathic pain, have shown that the central nervous system reacts to the algogen stimuli with a series of biochemical and physiopathological responses. This capability of the nervous system to functionally and morphologically adapt itself with algogen stimuli, is known as neuroplasticity and it has an essential role in inducing the onset or in maintaining the painful symptomatology.

Among the drugs used in the neuropathic pain treatment the carbamazepine has been widely used in clinical studies, and the results obtained have shown the efficacy of said drug in the treatment of trigeminal neuralgia, of the diabetic neuropathic pain and in the post-herpetic neuralgia. However the administration of this drug produces in patients marked side effects such as for example, somnolence, dizziness, ataxy, nausea and vomit, which limit the use thereof.

In these last years other drugs for the treatment of the neuropathic pain have been experimented. Among these, it is in particular mentioned gabapentin, which has a high analgesic efficacy for the neuropathic pain treatment, particularly the diabetic neuropathic pain and the post-herpetic pain. However the therapy with gabapentin causes side effects of central type such as somnolence, weariness, obesity, etc. (Martindale XXXth Ed. p. 374).

The need was therefore felt to have available drugs having in the treatment of the chronic pain, in particular neuropathic pain, an improved pharmacotherapeutic profile and/or lower side effects.

It has now been surprisingly and unexpectedly found that this technical problem can be solved with the class of drugs which is described hereunder.

An object of the present invention are nitrooxyderivative compounds or salts thereof having th following general formula (I):

$$A—(B)_{b0}—(C)_{c0}—NO_2 \quad \text{(I)}$$

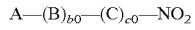

wherein:
c0 is an integer and is 0 or 1, preferably 1;
b0 is an integer and is 0 or 1, with the proviso that c 0 and b0 cannot be contemporaneously equal to zero;
$A=R—T_1—$, wherein R is the radical of an antipain drug for the chronic pain, in particular for the neuropathic pain;
$T_1=(CO)_t$ or $(X)_{t'}$, wherein $X=O$, S, $NR_{1c}$, $R_{1c}$ is H or a linear or branched alkyl, having from 1 to 5 carbon atoms, t and t' are integers and equal to zero or 1, with the proviso that t=1 when t'=0; t=0 when t'=1;
$B=—T_B—X_2—T_{BI}—$wherein
$T_B$ and $T_{BI}$ are equal or different;
$T_B=(CO)$ when t=0, $T_B=X$ when t'=0, X being as above;
$T_{BI}=(CO)_{tx}$ or $(X)_{txx}$, wherein tx and txx have the value of 0 or 1; with the proviso that tx=1 when txx=0; and tx=0 when txx=1; X is as above;
$X_2$, bivalent radical, is such that the corresponding precursor of $B—T_B—X_2—T_{BI}—$wherein the free valences of $T_B$ and of $T_{BI}$ are saturated each with OZ, with Z or with $—N(Z^I)(Z^{II})$, being:
Z=H, $C_1–C_{10}$, preferably $C_1–C_5$ alkyl linear or branched when possible,
$Z^I$, $Z^{II}$ equal to or different have the values of Z as above, depending on that $T_B$ and/or $T_{BI}=CO$ or X, in function of the values of t, t', tx and txx;
the precursor compound of B as above defined is preferably selected from the following classes of compounds:
aminoacids, selected from the following: L-carnosine, anserine, selenocysteine, selenomethionine, penicillamine, N-acetylpenicillamine, cysteine, N-acetylcysteine, glutathione or esters thereof, preferably ethyl or isopropyl ester;
hydroxyacids, selected from the following: gallic acid, ferulic acid, gentisic acid, citric acid, caffeic, dihydrocaffeic acid, p-cumaric acid, vanillic acid; aromatic and heterocyclic polyalcohols, selectd from the following: nordihydroguaiaretic acid, quercetin, catechin, kaempferol, sulfurethyne, ascorbic acid, isoascorbic acid, hydroquinone, gossypol, reductic acid, methoxyhydroquinone, hydroxyhydroquinone, propyl gallate, saccharose, 3,5-di-tertbutyl-4-hydroxybenzylthio glycolate, p-cumaric alcohol, 4-hydroxy-phenylethylalcohol, coniferyl alcohol, allopurinol;
compounds containing at least one free acid function, selected from the following: 3,3'-thiodipropionic acid, fumaric acid, dihydroxymaleic acid, edetic acid;
$C=$bivalent radical$—T_c—Y—$ wherein
when $b0=c0=1$: $T_c=(CO)$ when tx=0, $T_c=X$ when txx=0, X being as above defined,
when $b0=0$: $T_c=(CO)$ when t=0, $T_c=X$ when t'=0, X being as above defined,
when $c0=0$: tx=0, $T_{BI}=X=—O—$;
Y has one of the following meanings:
$Y_P$:

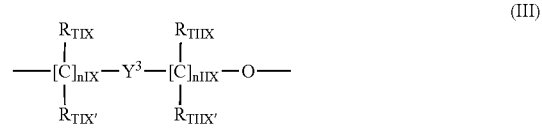

(III)

wherein:
nIX is an integer from 0 to 5, preferably 1;
nIIX is an integer from 1 to 5 preferably 1;

$R_{TIX}$, $R_{TIX}$, $R_{TIIX}$, $R_{TIIX}$, equal to or different from each other are H or linear or branched $C_1$–$C_4$ alkyl; preferably $R_{TIX}$, $R_{TIX}$, $R_{TIIX}$, $R_{TIIX}$, are H;

$Y^3$ is a saturated, unsaturated or aromatic heterocyclic ring having 5 or 6 atoms, containing from one to three heteroatoms, preferably from one to two, said heteroatoms being equal or different and selected from nitrogen, oxygen, sulphur;

or Y can be:

$Y_O$, selected from the following:

an alkylenoxy group R'O wherein R' is a linear or branched when possible $C_1$–$C_{20}$, having preferably from 2 to 6 carbon atoms, or a cycloalkylene having from 5 to 7 carbon atoms, in the cycloalkylene ring one or more carbon atoms can be substituted by heteroatoms, the ring can have side chains of R' type, R' being as above;

or Y is selected from one of the following groups:

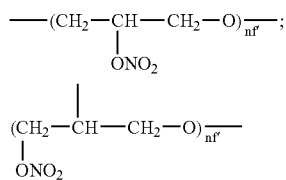

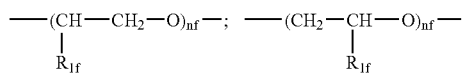

wherein nf' is an integer from 1 to 6 preferably from 1 to 4;

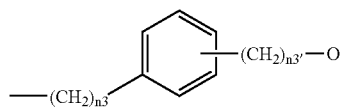

wherein $R_{1f}$=H, $CH_3$ and nf is an integer from 1 to 6; preferably from 2 to 4;

$Y_{AR}$, selected from:

$Y_{AR1}$:

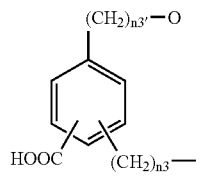

wherein n3 is an integer from 0 to 5 and n3' is an integer from 1 to 3; or $Y_{AR2}$:

(VI)

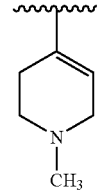

wherein n3 and n3' have the above meaning.

The radical R in formula (I) is preferably that of chronic analgesic drugs, in particular of drugs for the neuropathic pain, and it can be selected from the conventional compounds used for these applications. Tricyclic antidepressive drugs and antiepileptic drugs can be mentioned.

Preferably R is the radical of an analgesic drug, having formula II:

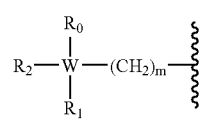

wherein:

W is a carbon atom or a nitrogen atom;

m is an integer from 0 to 2;

$R_0$=H, —$(CH_2)_n$—$NHR_{1A}$, n being an integer from 0 to 2, wherein $R_{1A}$=H, —C(O)—$R_{1H}$, —C(O)O—$R_{1H}$, wherein $R_{1H}$ is a linear or branched $C_1$–$C_{10}$ alkyl, a phenyl or benzyl group; or $R_{1H}$ has one of the following meanings:

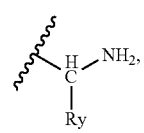

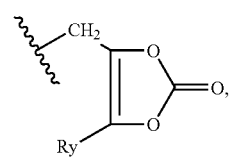

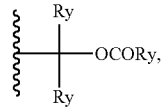

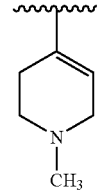

wherein Ry is hydrogen, a linear or branched $C_1$–$C_{10}$ alkyl, a phenyl or benzyl group;

$R_1$=H, when W=N, $R_1$ is the electronic doublet on the nitrogen atom (free valence);

$R_2$ is chosen between the following groups:

phenyl, optionally substituted with an halogen atom or with one of the following groups: —$OCH_3$, —$CF_3$, nitro;

mono- or di-hydroxy substituted benzyl, preferably 3-4 di-hydroxy substituted benzyl;

amidino group: $H_2N(C=NH)$—;

the radical of formula (IIA), wherein optionally one unsaturation of ethylene type can be present between the carbon atoms in position 1 and 2, or 3 and 4, or 4 and 5:

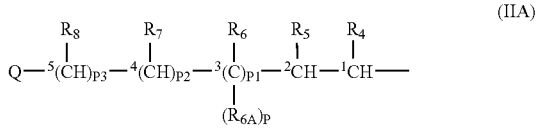

wherein:
p, $p_1$, $p_2$ are integers, equal to or different from each other and are 0 or 1;
$p_3$ is an integer from 0 to 10;
$R_4$ is hydrogen, linear or branched $C_1$–$C_6$ alkyl, free valence;
$R_5$ can have the following meanings:
  linear or branched $C_1$–$C_6$ alkyl,
  $C_3$–$C_6$ cycloalkyl,
  free valence,
  $OR_A$, wherein $R_A$ has the following meanings:
    linear or branched $C_1$–$C_6$ alkyl optionally substituted with one or more halogen atoms, preferably F,
    phenyl, optionally substituted with one halogen atom or with one of the following groups: —$OCH_3$, —$CF_3$, nitro;
$R_6$, $R_{6A}$, $R_7$, $R_8$, equal or different, are H, methyl; or free valence;
with the proviso that in the radical of formula (IIA) when one unsaturation of ethylene type between $C_1$ and $C_2$ is present, $R_4$ and $R_5$ are free valences such as to form the double bond between $C_1$ and $C_2$; when the unsaturation is between $C_3$ and $C_4$, $R_6$ and $R_7$ are free valences such as to form the double bond between $C_3$ and $C_4$; when the unsaturation is between $C_4$ and $C_5$, $R_7$ and $R_8$ are free valences such as to form the double bond between $C_4$ and $C_5$;
Q is equal to H, OH, $OR_B$ wherein $R_B$ is benzyl, a linear or branched $C_1$–$C_6$ alkyl, optionally substituted with one or more halogen atoms, preferably F, phenyl optionally substituted with one halogen atom or with one of the following groups: $OCH_3$, —$CF_3$, nitro;
or Q can have one of the following meanings:
  $C_3$–$C_6$ cycloalkyl;
  linear or branched $C_1$–$C_6$ alkyl;
  guanidine ($H_2NC(=NH)NH$—);
  thioguanidine ($H_2NC(=S)NH$—);
in formula (II) $R_2$ with $R_1$ and with W=C taken together form a $C_4$–$C_{10}$, preferably $C_6$, saturated or unsaturated, preferably saturated, ring.

When in formula (II) W=C, m=1 and $R_0$=—$(CH_2)_n$—$NH_2$ with n=1, $R_2$ and $R_1$ with W as above defined form together the cyclohexane ring, in the radical A of formula (I) $T_1$=CO and the free valence of A is saturated with OH, the precursor drug of R is known as gabapentine;

when in formula (II) W=C, m=0 and $R_0$=—$(CH_2)_n$—$NH_2$ with n=0, $R_1$=H, $R_2$ is the radical of formula (IIA) wherein p=$p_1$=1, $p_2$=$p_3$ =0, $R_4$=$R_5$=$R_6$=$R_{6A}$=H, Q=H, in the radical A of formula (I) $T_1$=CO and the free valence of A is saturated with OH, the precursor drug of R is known as norvaline;

when in formula (II) W=C, m=0 and $R_0$=—$(CH_2)$—$NH_2$ with n=0, $R_1$=H, $R_2$ is the radical of formula (IIA) wherein p=$p_1$=1, $p_2$=$p_3$ =0, $R_4$=$R_5$=$R_{6A}$=H, Q is the guanidine group, in the radical A of formula (I) $T_1$=CO and the free valence of A is saturated with OH, the precursor drug of R is known as arginine;

when in formula (II) W=C, m=0 and $R_0$=—$(CH_2)_n$—$NH_2$ with n=0, $R_1$=H, $R_2$ is the radical of formula (IIA) wherein p=$p_1$=1, $p_2$=$p_3$ =0, $R_4$=$R_5$=$R_6$=$R_{6A}$=H, Q is the thioguanidine group, in the radical A of formula (I) $T_1$=CO and the free valence of A is saturated with OH, the precursor drug of R is known as thiocitrulline;

when in formula (II) W=C, m=1 and $R_0$=—$(CH_2)_n$—$NH_2$ with n=1, $R_1$=H, $R_2$ is the radical of formula (IIA) wherein p =$p_1$=$p_2$=$p_3$=0, $R_4$=H, $R_5$=Q=$CH_3$, in the radical A of formula (I) $T_1$=CO and the free valence of A is saturated with OH, the precursor drug of R is known as pregabaline;

when in formula (II) W=C and has configuration (S), m=1 and $R_0$=—$(CH_2)_n$—$NH_2$ with n=1, $R_1$=H, $R_2$ is the radical of formula (IIA) wherein p=$p_1$=$p_2$=$p_3$=0, $R_4$=H, $R_5$=Q =$CH_3$, in the radical A of formula (I) $T_1$=CO and the free valence of A is saturated with OH, the precursor drug of R is known as (S) 3-isobutylGABA;

when in formula (II) W=C, m=1 and $R_0$=$R_1$=H, $R_2$ is the radical of formula (IIA) wherein p=$p_1$=1, $p_2$=$p_3$=0, $R_4$ =$R_5$=$R_6$=$R_{6A}$=H, Q is the guanidine group, in the radical A of formula (I) $T_1$=NH and the free valence of A is saturated with H, the precursor drug of R is known as agmatine;

when in formula (II) W=C, m=2 and $R_0$=—$(CH_2)_n$—$NH_2$ with n=0, $R_1$=H, $R_2$ is the radical of formula (IIA) wherein p=$p_1$=$p_2$=$p_3$=0, $R_4$ and $R_5$ are free valences and between $C_1$ and $C_2$ there is one ethylene unsaturation, Q=H, in the radical A of formula (I) $T_1$=CO and the free valence of A is saturated with OH, the percursor drug of R is known as vigabatrin;

when in formula (II) W=C m=0 and $R_1$=—$(CH_2)_n$—$NH_2$ with n =0, $R_1$=H, $R_2$ is the radical 3-4 di-hydroxy substituted benzyl, $T_1$=CO and the free valence of A is saturated with OH, the percursor drug of R is known as 2-amino-3-(3,4-dihydroxyphenyl)propanoic acid (dopa).

Other compounds used for the chrornic pain which can be used as precursors of A =R-$T_1$ in formula (I) are lamotrigine, topiramate, tiagabine, zonisamide, carbamazepine, felbamate, amineptine, amoxapine, demexiptiline, desipramine, nortriptyline, opipramol, tianeptine.

Generally the precursor drugs of R are synthesized according to the methods reported in "The Merck Index, 12th Ed." (1996). When the precursor drugs of R comprise in the molecule the radical of formula (IIA), they can be synthesized as described in patent application WO 00/76958.

The precursor compounds of B of the above groups are prepared according to the methods known in the prior art and described, for example, in "The Merck Index, 12th Ed." herein incorporated by reference.

Preferably when in formula (I) b0=0, Y in the bivalent linking group C is selected between $Y_P$ and $Y_{AR}$ as above defined.

Preferably $Y^3$ is selected from the following bivalent radicals:

(Y1)

(Y2)

-continued (Y3) 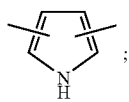

(Y4) 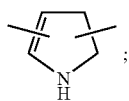

(Y5) 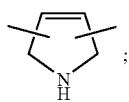

(Y6) 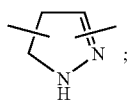

(Y7) 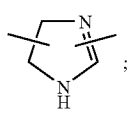

(Y8) 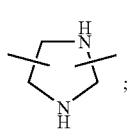

(Y9) 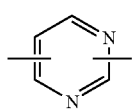

(Y10) 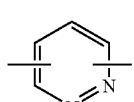

(Y11) 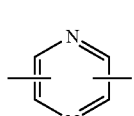

(Y12) 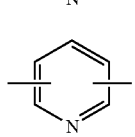

(Y13) 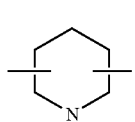

(Y14) 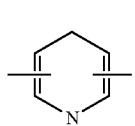

(Y15) 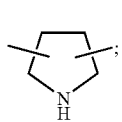

-continued (Y16) 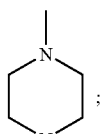

(Y17) 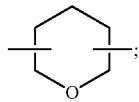

(Y18) 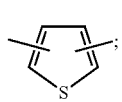

(Y19) 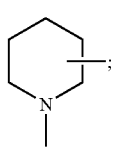

The preferred of $Y^3$ are the following: (Y12), having the two free valences in the ortho position with respect to the nitrogen atom; (Y16) with the two valences linked to the two heteroatoms, Y1 (pyrazol) 3,5-disubstituted; (Y19), wherein the free valence on the ring is found in para position to the nitrogen atom.

The precursors of Y as defined by formula (III), wherein the free valence of the oxygen is saturated with H and the free valence of the end carbon is saturated either with a carboxylic or hydroxyl group, are products available on the market or can be obtained by methods known in the prior art.

In formula (I) the preferred precursors of B for the synthesis of the nitrooxyderivatives usable in the present invention are the following: ferulic acid, N-acetylcysteine, cysteine, caffeic acid, hydrocaffeic and gentisic acid; the preferred precursor drugs are the following: gabapentine, norvaline, arginine, pregabaline, (S) 3-isobutylGABA, agmatine.

The preferred compounds of formula (I) according to the present invention are the following:

1-(aminomethyl)cyclohexan acetic acid 2-methoxy-4-[(1E)-3-[4-(nitrooxy) butoxy]-3-oxy-1-propenyl] phenyl hydrochloride ester (XV)

1-(aminomethyl)cyclohexan acetic acid
3-(nitrooxymethyl) phenyl hydrochloride ester
(XVI)

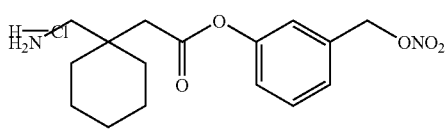

2-aminopentanoic acid 3-(nitrooxymethyl)phenyl
hydrochloride ester (XVII)

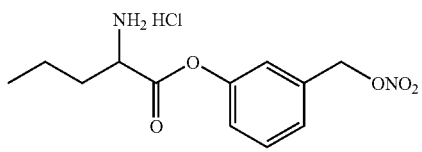

(S)-N-acetylcysteine-, 4-(nitrooxy)butyl ester,
2-amino hydrochloride pentanoate (XVIII)

(S)-N-acetylcysteine-, 4-(nitrooxy)butyl ester,
1-(aminomethyl)cyclohexanacetate hydrochloride
(XIX)

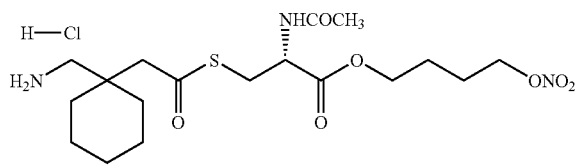

1-(aminomethyl)cyclohexanacetic acid-, [6-(nitrooxy methyl)-2-pyridinyl]methyl hydrocloride
ester (XX)

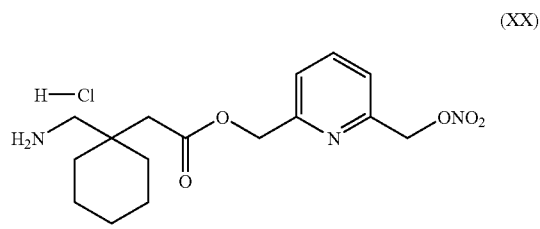

alpha-amino-delta-thioureidopentanoic acid,
3-(nitrooxy methyl)phenyl hydrocloride ester (XXI)

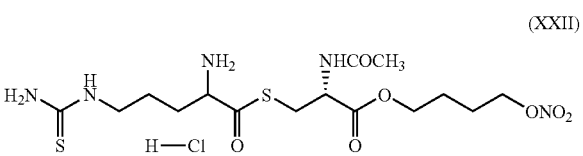

(S)-N-acetylcysteine-, 4-(nitrooxy)butyl ester,
alpha-amino-delta-thioureidopentanoate hydrocloride (XXII)

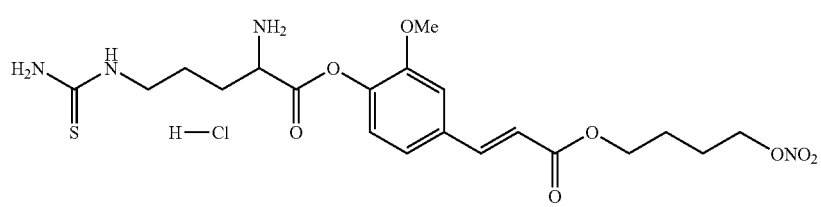

alpha-amino-delta-thioureidopentanoic acid,
2-methoxy-4-[(1E)-3-[4-(nitrooxy)butoxy]-3-oxy-1-propenyl]phenyl hydrocloride ester (XXIII)

(XXIII)

2-amino-5-guanidinopentanoic acid, 3-(nitrooxy
methyl)phenyl hydrocloride ester (XXIV)

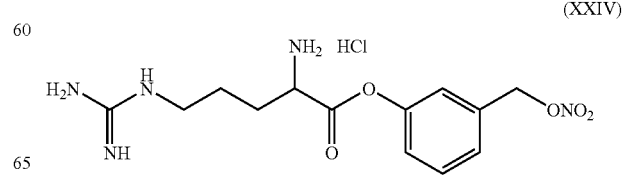

2-amino-5-guanidinopentanoic acid-, 2-methoxy-4-[(1E)-3-[4-(nitrooxy)butoxy]-3-oxy-1-propenyl]phenyl hydrocloride ester (XXV)

(XXV)

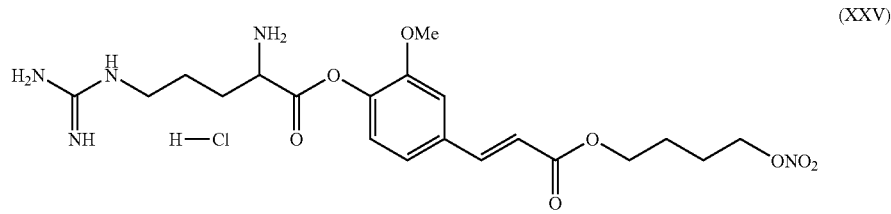

(S)-N-acetylcysteine-4-(nitrooxy)butyl ester, 2-amino-5-guanidinopentanoate hydrocloride (XXVI)

(XXVI)

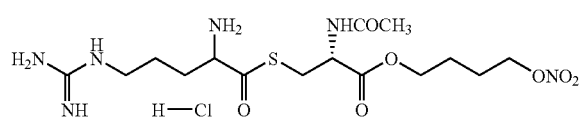

4-(guanidine)butyl-3-nitrooxymethylbenzamide (XXVII)

(XXVII)

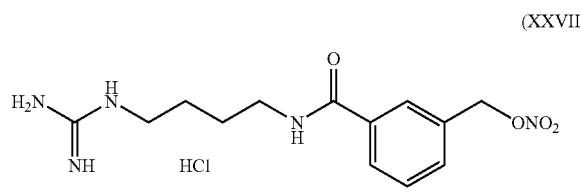

4-(guanidine)butyl-3-[4-(4'-nitrooxybutyryloxy)-3-(methoxy)]phenyl-2-propenamide chloride (XXVIII)

1-(aminomethyl)cyclohexan acetic acid 4-(nitroxy)butyl hydrochloride ester (XXIX)

(XXIX)

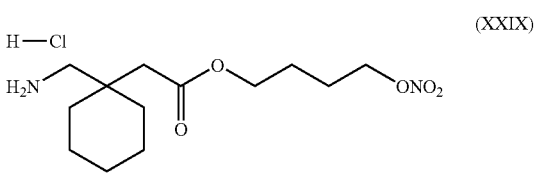

The preferred above compounds with formulas (XV) to (XXIX) can be used as nitrate salts.

The compounds according to the present invention, when they contain in the molecule one salifiable nitrogen atom, can be transformed into the corresponding salts by reaction in organic solvent such for example acetonitrile, tetrahydrofuran with an equimolar amount of the corresponding organic or inorganic acid.

Examples of organic acids are: oxalic, tartaric, maleic, succinic, citric acid.

Examples of inorganic acids are: nitric, hydrocloric, sulphuric, phosphoric acid.

Nitrate salts are preferred.

The compounds of the invention have shown to have an improved activity in the chronic pain treatment, in particular neuropathic, both at the central and peripheral nervous system level. Besides it has been surprisingly found by the Applicant that the invention compounds not only have an improved efficacy in reducing the neuropathic pain, but unexpectedly show also a lowering action of the progress of the pathological condition which causes the neuropathic (XXVIII)

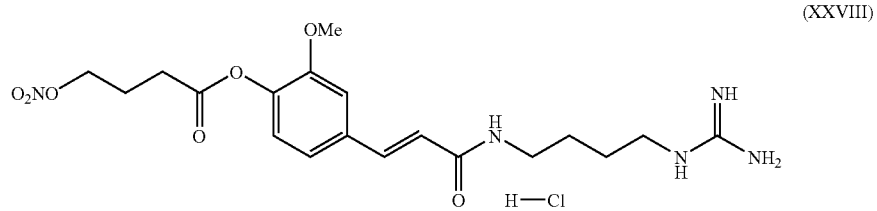

pain. For example when the drugs of the present invention are administered to diabetic patients for reducing the diabetic neuropathic pain, it has been found that they are able not only to reduce neuropathies, but also to reduce the complications caused by diabetes, for example affecting the blood vessels and/or the renal apparatus.

The compounds of the invention are particularly effective in the neuropathic pain treatment, for example the diabetic neuropathic pain, the post-infarct pain.

The compounds of the invention can also be used in combination or in admixture with NO-donor compounds of the prior art.

Said compounds contain for example in the molecule one or more $ONO_2$ or ONO groups.

The NO-donor compounds which can be used in combination with the invention compounds must comply with the test in vitro defined hereinafter.

The test relates to the nitric oxide generation from the NO-donors, for example nitroglycerin, niocorandil, nitroprussiate, etc., in the presence of endothelial cells (method a) or platelets (method b).

a) Endothelial Cells

Human cells of the umbilical vein, cultured on plates, having a $10^3$ density cells/well were incubated for 5 minutes with scalar concentrations of NO-donor (1–100 μg/ml). The incubation medium (physiologic solution, for example Tyrode) was then analyzed to determine the capability to generate NO of the compound under test, by means of:
1) nitric oxide detection by chemiluminescence;
2) cGMP determination (cyclic GMP n° 2715 of the above mentioned Merck).

For the analysis by chemiluminescence, an amount equal to 100 μl was injected in the reaction chamber of a chemiluminescence analyzer containing glacial acetic acid and potassium iodide. The nitrites/nitrates present in the medium, under these conditions are converted into NO which is then detected after reaction with ozone, wich produces light. In the equipments which measure the chemiluminescence, the luminescence produced is directly proportional to the generated NO levels and can be measured by a suitable photomultiplying unit of a chemiluminescence analyzer. The photomultiplier converts the incident light in electric voltage, which is quantitatively recorded. On the basis of a calibration curve, prepared with scalar nitrite concentrations, it can be quantitatively determined the generated NO amount. For example, from the incubation of 100 μM of nicorandil, an amount equal to about 10 μM of NO was generated.

For cGMP determination, an aliquot of the incubation medium (equal to 100 μl) was centrifuged at 1,000 revolutions per 20 seconds. The surnatant was removed and the sediment treated with iced phosphate buffer (pH 7.4). The cGMP levels produced were tested by specific immuno-enzymatic reactants. From said experiments it resulted that, under these experimental conditions, the incubation with one of the various tested NO-donors caused a significant increase of cGMP with respect to the values obtained in absence of a NO-donor. For example, after an incubation with 100 μM of sodium nitroprussiate, an increase of about 20 times the value obtained with the incubation of the carrier alone without NO-donor was recorded.

b) Platelets

Washed human platelets, prepared substantially in the same way as described by Radomski et al, (Br. J. Pharmacol. 92, 639-1987), were used. 0.4 ml aliquots were incubated with NO-donor scalar concentrations (1–100 μg/ml) for 5 minutes. The incubation medium (for example Tyrode) was then analyzed to determine the capability of the tested compound to generate NO, by determination of nitric oxide by chemiluminescence and the cGMP determination, as described in the previous paragraph for the same analyses carried out on endothelial cells. For the determination by chemiluminescence, also in this case, on the basis of a calibration curve prepared with scalar nitrite concentrations, it was possible to quantitatively determine the produced NO amount. For example, after an incubation of 100 μM of nicorandil, an amount equal to 35 μM of NO was generated.

For cGMP determination, it resulted that also in these experimental conditions the incubation with one of the tested NO-donors gave a significant increase of cGMP with respect to the values obtained in absence of a NO-donor. For example, after an incubation with 100 μM of sodium nitroprussiate, an increase of about 30 times the value obtained with the incubation of the only carrier without NO-donor, was recorded.

The preferred NO-donor compounds are those containing in the moelcule radicals of drugs belonging to the classes of aspirin, ibuprofen, paracetamol, naproxen, diclofenac, flurbiprofen. The syntheses of these preferred compounds are described in patent applications WO 95/30641, WO 97/16405, WO 95/09831, WO 01/12584.

The compounds of the invention can be obtained by the methods described hereafter.

If in the drug molecule more reactive groups such for example COOH and/or HX are present, they must be usually protected before the reaction according to the methods known in the prior art; for example as described in the volume by Th. W. Greene: "Protective groups in organic synthesis", Harward University Press, 1980.

The acylhalides are prepared according to the methods known in the prior art, for example by thionyl or oxalyl chloride, halides of $P^{III}$ or $P^V$ in solvents inert under the reaction conditions, such as for example toluene, chloroform, DMF, etc.

1) When in formula (I) b0=0 and the free valence of the radical R of the drug is saturated with a carboxylic group, the synthesis methods to obtain the corresponding nitrooxyderivatives are the following:

1.A) The drug of formula RCOOH is treated with an agent activating the carboxyl group selected from N,N'carbonyldi imidazol (CDI), N-hydroxybenzotriazol and dicyclohexylcarbodiimide (DCC) in solvent such as for example DMF, THF, chloroform, etc., at a temperature in the range from −5° C. to 50° C. and reacted in situ with a compound HO—Y—Hal, wherein Y and Hal are as above defined.

(1C)

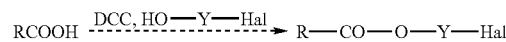

1.B) In alternative, the drug acylhalide is reacted with a compound HO—Y—$R_{8A}$, wherein Y is as above, $R_{8A}$ is OH or a halogen in the presence of a base, in an organic solvent inert under the reaction conditions according to the scheme below reported:

(1D)

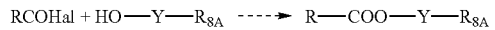
RCOHal + HO—Y—$R_{8A}$ ----▶ R—COO—Y—$R_{8A}$

1.C) When the compounds obtained in the above reactions have formula R—COO—Y—Hal the corresponding nitrooxyderivatives are obtained by reacting the compound R—CO—O—Y—Hal with $AgNO_3$ in organic solvent such as acetonitrile, tetrahydrofuran according to the scheme:

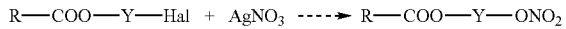
R—COO—Y—Hal + $AgNO_3$ ----▶ R—COO—Y—$ONO_2$

1.D) When the compounds obtained in the above reactions have formula R—COO—Y—OH the hydroxyl group is subjected to halogenation, for example with $PBr_3$, $PCl_5$, $SOCl_2$, $PPh_3+I_2$, and then reacted with $AgNO_3$ in organic solvent such as acetonitrile, tetrahydrofuran.

2) When in formula (I) b0=0, and the reactive function of the drug is the group $NH_2$, the synthesis methods to obtain the corresponding nitrooxyderivatives are the following:

2.a) By reaction of the drug R—$NH_2$ with an acyl halide of formula Hal—Y—COHal, wherein Y and Hal are as above, according to the scheme:

(2A)

R—$NH_2$ + Hal—Y—COHal ----▶ R—NHCO—Y—Hal 2.b) By reaction of the drug R—$NH_2$ with an acyl halide of formula OH—Y—COHal, wherein Y and Hal are as above, according to the scheme:

(2B)

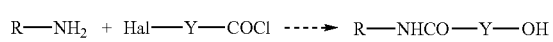
R—$NH_2$ + Hal—Y—COCl ----▶ R—NHCO—Y—OH 2.c) When the compounds obtained in the above reactions have formula R—NHCO—Y—Hal or R—NHCO—Y—OH the corresponding nitrooxyderivatives are obtained as above described in 1.C and 1.D respectively.

3. When in formula (I) b0=c0=1, and the free valence of the radical R of the drug is saturated with a carboxylic group, the synthesis methods to obtain the corresponding nitrooxyderivatives are the following:

3.a) Alternatively, the acyl halide of the drug and the compound of formula HX—$X_2$—COOH, wherein X and $X_2$ are as above, are reacted according to the methods known in the prior art, to give the compound R—CO—X—$X_2$—COOH which is transformed into the corresponding sodic salt and reacted with a compound of formula Hal—Y—$R_8$ wherein Hal and Y are as above and $R_8$ is Cl, Br, Iodine, OH:

(3.A)

R—COHal + HX—$X_2$—COOH ----▶
R—CO—X—$X_2$—COOH (3.A')

R—CO—X—$X_2$—COONa + Hal—Y—$R_{8A}$ ----▶
R—CO—X—$X_2$—CO—Y—$R_{8A}$

When $R_{8A}$=OH the compound of formula (3.A') is subjected to halogenation as above described in 1.D; when $R_{8A}$=Hal the compound of formula (3.A') is reacted with $AgNO_3$ in organic solvent such as acetonitrile, tetrahydrofuran:

3.b) When $Y_T$ is a $C_4$ linear alkylene, the precursor of B of formula HO—$X_2$—COOH is reacted with triphenylphosphine in the presence of a halogenating agent such as $CBr_4$ or N-bromosuccinimide in tetrahydrofuran to give the compound of formula HO—$X_2$—$COO(CH_2)_4Br$ which is reacted with the molecule of the drug RCOOH as described in 1.A and 1.C.

4) When in formula (I) p=1 b0=c0=1, and the reactive function of the drug is the group $NH_2$, the synthesis methods to obtain the corresponding nitrooxyderivatives are the following:

4.a) Reaction of the drug R—$NH_2$ with an acyl halide of formula HX—$X_2$—COHal, wherein X and $X_2$ are as above, according to the methods known in the prior art, to give the compound R—NH—CO—$X_2$—XH which is reacted with a compound of formula $R_{8A}$—Y—COHal wherein $R_{8A}$ and Y are as above.

(4.A)

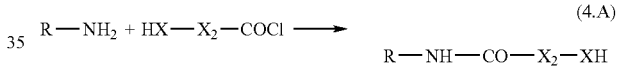
R—$NH_2$ + HX—$X_2$—COCl ⟶
R—NH—CO—$X_2$—XH (4A')

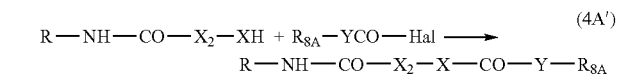
R—NH—CO—$X_2$—XH + $R_{8A}$—YCO—Hal ⟶
R—NH—CO—$X_2$—X—CO—Y—$R_{8A}$ 4.b) Alternatively, the drug R—$NH_2$ is reacted with a compound of formula HX—$X_2$—COOH, wherein X and $X_2$ are as above, in the presence of dicyclohexylcarbodiimide as described in 1.A, to give the compound R—NH—CO—$X_2$—XH, which is reacted with a compound of formula $R_{8A}$—Y—COCl wherein $R_{8A}$ and Y are as above defined, to give the following compound: R—NH—CO—$X_2$—X—CO—Y—$R_{8A}$ (4.B)When $R_{8A}$=OH the compound of formula (4.B) or of formula (4a') is subjected to halogenation as above described in 1.D; when $R_{8A}$=Hal the compound of formula (4.B) is reacted with $AgNO_3$ in organic solvent such as acetonitrile, tetrahydrofuran.

When the compounds of the present invention have one or more chiral centres, they can be used in a racemic form, as mixtures of diastereoisomers or enantiomers, as single enantiomers or single diastereosisomers. If the compound shows geometric asymmetry, the compound in the cis or trans form can be used.

The compounds object of the present invention are formulated in the corresponding pharmaceutical compositions for pareneteral, oral and topical use according the techniques well known in the field, together with the usual excipients, see for example the volume "Remington's Pharmaceutical Sciences 15th Ed."

The amount on a molar basis of the active principle in said formulations is the same or lower than the maximum posology indicated for the precursor drugs. Also higher doses can be used, considering their very good tolerability.

The daily administrable doses are those of the precursor drugs, or in case lower. The daily doses can be found in the publications of the field, such as for example in "Physician's Desk reference".

A further object of the invention is the use of analgesic drugs for the treatment of the chronic pain, in particular the neuropathic pain, in combination with NO-donor compounds as above defined.

The radicals of the conventional analgesic drugs for the chronic pain have been indicated above with R wherein the free valence is saturated with $T_{1A}$, wherein $T_{1A}=COZ_1$ wherein $Z_1. =SH$, $OZ$, $NHR_{1C}$, $XZ$, wherein $Z$, $R_{1C}$ and $X$ are as above defined.

Said compounds of formula $RCOZ_1$ are the precursor drugs of R.

It has been found that the combination of the precursor drugs of R in combination with the NO-donor compounds shows a synergic effect, whereby it is possible to use a lower amount of the analgesic compound for the chronic pain, whereby the side effects are reduced.

Besides the above mentioned precursor drugs of R, the following ones can be mentioned: lamotrigine, topiramate, tiagabime, zonisamide, carbamazepine, felbamate, amineptine, amoxapine, demexiptiline, desipramine, nortriptyline, opipramol, tianeptine, amitriptyline, butriptyline, clomipramine, dibenzepin, dimetacrine, dothiepin, doxepin, fluacizine, imipramine, iprindole, lofepramine, melitracen, noxiptilin, propizepine, protriptyline, trimipramine.

The NO-donor compounds are as above defined.

The following Examples illustrate the invention without limiting the scope thereof.

EXAMPLE 1

Synthesis of the 1-(aminomethyl)cyclohexan acetic acid 2-methoxy-4-[(1E)-3-[4-(nitrooxy) butoxy]-3-oxy-1-propenyl]phenyl hydrochloride ester (XV)

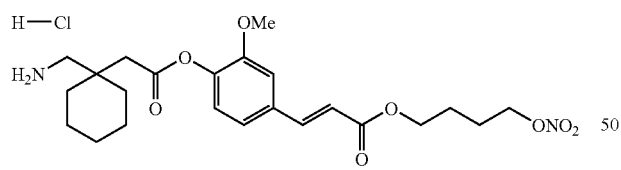

A) Synthesis of the 1-(N-tert-butoxycarbonylaminomethyl) cyclohexan acetic acid

To a solution of 1-(aminomethyl)cyclohexanacetic acid (10 g, 58.4 mmoles) in a mixture of dioxane (100 ml) and water (150 ml), triethylamine (16.27 ml, 116.8 mmoles) and di-tert-butyldicarbonate (15.3 g, 70 mmoles) are added. The reaction mixture is left at room temperature, under stirring for 4 hours. After the solution has been cooled to 0° C. it is brought to pH 2 with HCl 5%. The precipitate is filtered and dried under vacuum. 15 g of the expected product are obtained as a white solid having m.p.=125°–127° C.

B) Synthesis of 2-methoxy-4-[(1E)-3-[4-(bromo) butoxy]-3-oxy-1-propenyl]phenol

To a solution of ferulic acid (11.6 g, 59.7 mmoles) in tetrahydrofuran (400 ml) tetrabromomethane (39.62 g, 119.47 mmoles) and triphenylphosphine (31.34 g, 119.47 mmoles) are added. The obtained mixture is kept under stirring at room temperature for 5 hours, filtered and evaporated at reduced pressure. The crude residue is purified by chromatography on silica gel eluting with n-hexane/ethyl acetate 7/3. 8 g of the expected compound are obtained as a yellow solid having m.p.=86°–89° C.

C) Synthesis of 2-methoxy-4-[(1E)-3-[4-(nitrooxy) butoxy]-3-oxy-1-propenyl]phenol To a solution of 2-methoxy-4-[(1E)-3-[4-(bromo) butoxy]-3-oxy-1-propenyl]phenol (8 g, 24.3 mmoles) in acetonitrile (500 ml) silver nitrate (12.25 g, 72.9 mmoles) is added. The reaction mixture is heated at 40° C. for 12 hours sheltered from light. The formed salt is removed by filtration and the solution is evaporated at reduced pressure. The residue is purified by chromatography on silica gel eluting with n-hexane/ethyl acetate 75/25. 4 g of the expected product are obtained as a yellow solid having m.p.=65°–68° C.

D) Synthesis of the 1-(N-tert-butoxycarbonylaminomethyl) cyclohexan acetic acid 2-methoxy-4-[(1E)-3-[4-(nitrooxy)butoxy]-3-oxy-1-propenyl]phenyl ester To a solution of 1-(N-tert-butoxycarbonyl aminomethyl) cyclohexan acetic acid (2.5 g, 9.2 mmoles) in chloroform (200 ml) and N,N-dimethylformamide (3 ml), 2-methoxy-4-[(1E)-3-[4-(nitrooxy) butoxy]-3-oxy-1-propenyl] phenol (3.15 g, 10.1 mmoles), dicyclohexylcarbodiimide (5.7 g, 27.6 mmoles) and N,N-dimethylaminopyridine (33 mg, 0.27 mmoles) are added.

The reaction mixture is left at room temperature for 3 hours under stirring, filtered and evaporated at reduced pressure. The obtained residue is treated with ethyl acetate and washed with water. The organic phase is dried with sodium sulphate and evaporated at reduced pressure. The residue is purified by chromatography on silica gel eluting with n-hexane/ethyl acetate 9/1.5 g of the expected compound are obtained as an oil.

E) Synthesis of the 1-(aminomethyl)cyclohexan acetic acid 2-methoxy-4-[(1E)-3-[4-(nitrooxy) butoxy]-3-oxy-1-propenyl]phenyl hydrochloride ester To a solution of 1-(N-tert-butoxycarbonylamino methyl) cyclohexan acetic acid 2-methoxy-4-[(1E)-3-[4-(nitrooxy) butoxy]-3-oxy-1-propenyl]phenyl ester (5 g, 8.8 mmoles) in ethyl acetate (100 ml) a solution HCl 1N in ethyl acetate (50 ml) is added. The reaction mixture is left overnight at room temperature, then concentrated under vacuum to a volume of 40 ml. The obtained residue is treated with ethyl ether. The precipitate is filtered and dried under vacuum. 1.8 g of the expected compound are obtained as a white solid having m.p.=103°–105° C.

$^1$H-NMR (CDCl$_3$) ppm: 8.43 (2H, m); 7.55 (1H, d); 7.10 (3H, m); 6.34 (1H, d); 4.51 (2H, t); 4.26 (2H, t); 3.89 (3H, s); 3.12 (2H, s); 2.81 (2H, s); 1.82 (4H, m); 1.54 (10H, m).

EXAMPLE 2

Synthesis of the 1-(aminomethyl)cyclohexan acetic acid 4-(nitrooxy)butyl hydrochloride ester

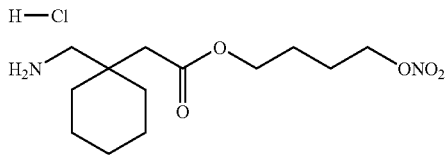

A) Synthesis of the 1-(N-tert-butoxycarbonylaminomethyl) cyclohexan acetic acid 4-(bromo)butyl ester To a solution of 1-(N-tert-butoxycarbonyl aminomethyl) cyclohexan acetic acid (1 g, 3.6 mmoles) in N,N-dimethyl formamide (50 ml) cooled at 0° C., sodium ethylate (246 mg, 3.6 mmoles) is added.

The reaction mixture is left at 0° C. under stirring for 30 minutes and then 1,4-dibromobutane (1.28 ml, 10.8 mmoles) is added. The solution is left under stirring overnight at room temperature, then diluted with ethyl ether and washed with water. The organic phase dried with sodium sulphate is evaporated under vacuum. The obtained residue is purified by chromatography on silica gel eluting with n-hexane/ethyl acetate 8/2. 0.7 g of the expected compound are obtained as an oil.

B) Synthesis of the 1-(N-tert-butoxycarbonylaminomethyl) cyclohexan acetic acid 4-(nitrooxy)butyl ester To a solution of 1-(N-tert-butoxycarbonylamino methyl) cyclohexan acetic acid 4-(bromo)butyl ester (1 g, 2.5 mmoles) in acetonitrile (200 ml), silver nitrate (1.3 g, 7.5 mmoles) is added. The reaction mixture is heated at 80° C. for 6 hours sheltered from light. The formed salt is removed by filtration and the solution is evaporated at reduced pressure. The residue is purified by chromatography on silica gel eluting with n-hexane/ethyl acetate 8/2. 0.8 g of the expected compound are obtained as an oil.

C) Synthesis of the 1-(aminomethyl)cyclohexan acetic acid 4-(nitrooxy)butyl hydrochloride ester To a solution of 1-(N-tert-butoxycarbonylamino methyl) cyclohexan acetic acid 4-(nitrooxy)butyl ester (0.8 g, 2.06 mmoles) in ethyl acetate (5 ml), a HCl 1N solution in ethyl acetate (20 ml) is added. The reaction mixture is left for 3 hours at room temperature then is treated with n-hexane. The precipitate is filtered and dried under vacuum. 0.45 g of the expected compound are obtained as a white solid having m.p.=80.3°–81.3° C.

$^1$H-NMR (DMSO) ppm: 8.23 (2H, s); 4.58 (2H, t); 4.09 (2H, t); 2.92 (2H, s); 2.56 (2H, s); 1.74 (4H, m); 1.44 (10H, m).

EXAMPLE 3

Synthesis of the 1-(aminomethyl)cyclohexan acetic acid 3-(nitrooxymethyl)phenyl hydrochloride ester (XVI)

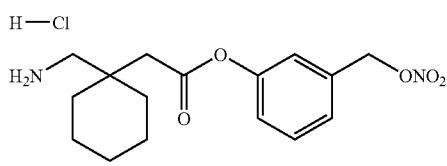

A) Synthesis of 3-(bromomethyl)phenol

To a solution of 3-hydroxybenzyl alcohol (4 g, 32.2 mmoles) in methylene chloride (250 ml), cooled at 0° C., tetrabromomethane (12.82 g, 38.6 mmoles) and triphenylphosphine (12.67 g, 48.3 mmoles) are added. The mixture is kept under stirring at 0° C. for 10 minutes, then evaporated at reduced pressure. The crude product is purified by chromatography on silica gel eluting with n-hexane/ethyl acetate 8/2. 3.5 g of the expected compound are obtained.

B) Synthesis of the 1-(N-tert-butoxycarbonylamino methyl)cyclohexan acetic acid 3-(bromomethyl) phenyl ester To a solution of 1-(N-tert-butoxycarbonylamino methyl) cyclohexan acetic acid (2.6 g, 9.7 mmoles) in chloroform (200 ml) and N,N-dimethylformamide (2 ml), 4-(bromomethyl)phenol (2 g, 10.7 mmoli), dicyclohexylcarbodiimide (4 g, 19.7 mmoles) and N,N-dimethylaminopyridine (24 mg, 0.20 mmoles) are added. The reaction mixture is left at room temperature for 4 hours under stirring, filtered and evaporated at reduced pressure. The obtained residue is treated with ethyl acetate and washed with water. The organic phase is dried with sodium sulphate and evaporated at reduced pressure. The obtained residue is purified by chromatography on silica gel eluting with n-hexane/ethyl acetate 9/1. 1.4 g of the compound are obtained as an oil.

C) Syynthesis of the 1-(N-tert-butoxycarbonylamino methyl)cyclohexan acetic acid 3-(nitrooxymethyl)phenyl ester To a solution of 1-(N-tert-butoxycarbonylamino methyl) cyclohexan acetic acid 3-(bromomethyl) phenyl ester (1.4 g, 3.18 mmoles) in acetonitrile (300 ml) silver nitrate (1 g, 6.36 mmoles) is added. The reaction mixture is heated at 50° C. for 4 hours sheltered from light. The formed salt is removed by filtration and the solution is evaporated at reduced pressure. The obtained residue is purified by chromatography on silica gel eluting with n-hexane/ethyl acetate 8/2. 0.75 g of the expected compound are obtained as an oil.

D) Synthesis of the 1-(aminomethyl)cyclohexan acetic acid 3-(nitrooxymethyl)phenyl hydrochloride ester To a solution of 1-(N-tert-butoxycarbonylamino methyl) cyclohexan acetic acid 3-(nitrooxymethyl)phenyl ester (0.75 g, 1.8 mmoles) in ethyl acetate (5 ml), a HCl 1N solution in ethyl acetate (18 ml) is added. The reaction mixture is left for 15 minutes at room temperature, then it is treated with n-hexane. The precipitate is filtered and dried under vacuum. 0.45 g of the expected compound are obtained as a white solid having m.p.=106°–108° C.

$^1$H-NMR (DMSO) ppm: 8.16 (3H, m); 7.52 (1H, t); 7.44 (1H,d); 7.34 (1H, s); 7.28 (1H, d); 5.65 (2H, s); 3.03 (2H, m); 2.86 (2H, s); 1.55 (10H, m).

EXAMPLE 4

Synthesis of the 2-aminopentanoic acid 2-methoxy-4-[(1E)-3-[4-(nitrooxy) butoxy]-3-oxy-1-propenyl] phenyl hydrochloride ester

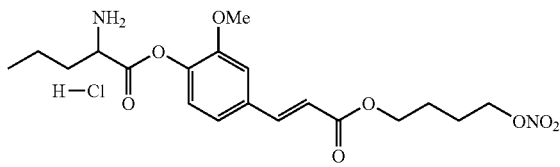

A) Synthesis of the 1-(N-tert-butoxycarbonylamino) pentanoic acid

To a solution of 2-aminopentanoic acid (4 g, 34.14 mmoles) in dioxane (40 ml) and water (75 ml), triethylamine (9.5 ml, 68.29 mmoles) and di-tert-butyldicarbonate (8.94 g, 49.97 mmoles) are added. The reaction mixture is left at room temperature, under stirring for 17 hours. After having cooled the solution at 0° C., it is brought to pH=2 with HCl at 5%. It is extracted with ethyl acetate, the joined organic phases are washed with water and dried with sodium sulphate.

The solvent is evaporated at reduced pressure to give the compound as an yellow oil which is used without further purification.

B) Synthesis of 2-methoxy-4-[(1E)-3-[4-(bromo) butoxy]-3-oxy-1-propenyl]phenol

To a solution of ferulic acid (11.6 g, 59.7 mmoles) in tetrahydrofuran (400 ml), tetrabromomethane (39.62 g, 119.47 mmoles) and triphenylphosphine (31.34 g, 119.47 mmoles) are added. The obtained mixture is kept under stirring at room temperature for 5 hours, filtered and evaporated at reduced pressure. The obtained crude compound is purified by chromatography on silica gel eluting with n-hexane/ethyl acetate 7/3.8 g of the expected compound are obtained as a yellow solid having m.p. =86° –89° C.

C) Synthesis of 2-methoxy-4-[(1E)-3-[4-(nitrooxy) butoxy]-3-oxy-1-propenyl]phenol To a solution of 2-methoxy-4-[(1E)-3-[4-(bromo) butoxy]-3-oxy-1-propenyl]phenol (8 g, 24.3 mmoles) in acetonitrile (500 ml) silver nitrate (12.25 g, 72.9 mmoles) is added. The reaction mixture is heated at 40° C. for 12 hours sheltered from light. The formed salt is removed by filtration and the solution is evaporated at reduced pressure. The obtained residue is purified by chromatography on silica gel eluting with n-hexane/ethyl acetate 75/25.4 g of the expected compound are obtained as a yellow solid having m.p.=65°–68° C.

C) Synthesis of the 2-(N-tert-butoxycarbonylamino) pentanoic acid 2-methoxy-4-[(1E)-3-[4-(nitrooxy) butoxy]-3-oxy-1-pro-penyl]phenyl ester To a solution of 2-(N-tert-butoxycarbonylamino) pentanoic acid (0.5 g, 2.3 mmoles) in chloroform (12 ml), 2-methoxy-4-[(1E)-3-[4-(nitrooxy) butoxy]-3-oxy-1-propenyl]phenol (0.86 g, 2.76 mmoles), dicyclohexylcarbodiimide (0.52 g, 2.53 mmoles) and N,N-dimethylaminopyridine (0.03 g, 0.23 mmoles) are added. The reaction mixture is left at room temperature for 1 hour under stirring, filtered and evaporated at reduced pressure. The obtained residue is purified by chromatography on silica gel eluting with n-hexane/ethyl acetate 75/25. 0.5 g of the expected compound are obtained as an oil. Yield 43%.

D) Synthesis of the 2-aminopentanoic acid 2-methoxy-4-[(1E)-3-[4-(nitrooxy)butoxy]-3-oxy-1-propenyl]phenyl hydrocloride ester To a solution of 2-(N-tert-butoxycarbonylamino) pentanoic acid 2-methoxy-4-[(1E)-3-[4-(nitrooxy)butoxy]-3-oxy-1-propenyl]phenyl ester (0.28 g, 0.548 mmoles) in ethyl acetate (7 ml), a HCl solution in ethyl acetate (6.8 N, 0.700 ml) is added. The reaction mixture is left 3 hours at room temperature. The precipitate is filtered and dried under vacuum. 0.1 g, of the expected compound are obtained as a white solid.

$^1$H-NMR (DMSO) ppm: 8.75 (3H, m); 7.62 (1H, d); 7.58 (1H, s); 7.3 (1H, d); 7.2 (1H, d); 6.72 (1H, d); 4.57 (2H, t); 4.26 (1H, t); 4.18 (2H, t); 3.82 (3H, s); 1.95 (2H, m); 1.75 (4H, m); 1.45 (2H, m); 0.98 (3H, m).

EXAMPLE F 1

Evaluation of the Analgesic Activity of the Invention Compounds by the "Paw-Licking" Test Four groups of Swiss male mice (20–25 g, Charles River) each formed by 10 animals, received by intraperitoneal injection Gabapentin (90 mg/kg) or the compound of formula (XVI) (Example 3), called NO-Gabapentin at the doses of 50 mg/kg, in a saline solution. The control group received the same volume of saline solution. One hour after the administration of the compound solutions, formalin (10 μl) was injected in the paw. In the 15 minutes subsequent to formalin administration, for each animal, the number of times wherein it licked its paw was counted. The analysis was carried out "in blind".

The results reported in Table 1 are expressed as percentage ratio between the number of times wherein the "paw-licking" was observed in the treated animals to that of the control group.

The results show that the NO-gabapentin is more active than the starting drug in inhibiting the "paw-licking".

EXAMPLE F 2

Evaluation of the Analgesic Activity of the Drugs used in the Chronic (Neuropathic) Pain Treatment Combined with a Nitric Oxide-donor Drug.

Wistar adult rats weighing about 200 grams were used, in the experimental model described by Bennett G J, Xie Y K, Pain 1988, 33(1): 87–107. The pain response (withdrawal latencies) is determined 14 days after the ligature of the right sciatic nerve. The results obtained are reported in Table 2 and have been expressed as a percentage ratio of the difference between the response from the intact paw and from the injured paw, to the response of the control animals, that have been injected with the carrier and undergone the nerve ligature. The groups were of 10 rats each. The animals in each of the treated groups received, respectively, the following drugs at the indicated doses:

clomipramine 10 mg/kg i.p., 2-acetylsalicylic acid (3-nitrooxymethyl)phenyl ester (ASA-NO) 100 mg/Kg p.o.

clomipramine +NO-ASA at the above indicated doses.

NO-ASA was prepared as described in patent application WO 97/16405.

The results are reported in Table 2 and show that the mixture of the analgesic drug with the nitrooxyderivative synergically increases the analgesic effect.

EXAMPLE F 3

Acute Toxicity of Gabapentin and NO-Gabapentin in the Diabetic Animal

In 50 Wistar adult male rats weighing 165–190 g, diabetes was induced by injection i.v. of a single dose of streptozocin (65 mg/kg in 1 ml/kg buffer citrate at pH 4.5).

After one week the animals were distributed in three groups of 10 rats each and treated per os for three days with daily doses of 100 mg/kg of gabapentin and NO-gabapentin. The controls were treated only with streptozocin.

Death rate was monitored for 7 days from the last treatment.

The results are indicated in Table 3.

The Table shows that death rate in the diabetic animals administered with NO-gabapentin is less than half with respect to the animals treated with gabapentin.

EXAMPLE F 4

In this experiment the effect of acute administration of NO-gabapentin was assessed and compared with that of the precursor drug, gabapentin, in a rat model of neuropathic pain.

In 6 groups of female Sprague-Dawley rats weighting 200 g, photochemically-induced ischemic spinal cord injury was produced according to methods described by Xu et al. Pain, 1992, 48, 279–290. Spinally-injured rats developed a chronic pain syndrome, including marked mechanical and cold allodynia. The rats were injured 3–6 months before the beginning of the experiment.

Each group of rats was i.p. treated, respectively, with one of the following compounds using one of the above indicated doses:

NO-gabapentin at doses of 20 mg/Kg (55 mole/Kg), or 60 mg/Kg (167,21 μmole/Kg), or 100 mg/kg (278,7 μmole/Kg), dissolved in saline, single dose, i. p.);

gabapentin at doses of 30 mg/Kg (175 μmole/Kg) or 100 mg/kg (584 μmole/Kg), dissolved in saline, single dose i. p.);

the control group received the vehicle;

The response to cold was tested by spray-applying ethyl chloride on the shaved allodynic skin area at time 0(i.p. injection) and then at 30', 120' and 240'. The response was evaluated according to the following score:

0=no response;

1=localized response (skin twitch and contraction), no vocalization;

2=transient vocalization, moderate struggle;

3=sustained vocalization and aggression.

The results are reported in Table 4 and show that acute administration of NO-gabapentin alleviated in a dose-dependent way cold allodynia.

The effect of the compounds on motor activity was also evaluated using a combined testing system as described in Hao, J. X. and Xu, X. J., Pain, 1996, 66, 279–286.

Table 5 reports the results on motor performance of the same groups of rats i.p. injected.

When the score found in the treated group is comparable to that of the control groups it means that the animals of the treated group are not impaired as to motor activity and are not sedated.

Comments on Tables 4 and 5

Table 4 shows that the effect of NO-gabapentin was significant and lasted 120 min with the dose of 60 mg/kg (167,21 μmole/Kg) and 240 min with the dose of 100 mg/kg (278,7 μmole/Kg). The vehicle produced no effect. Gabapentin at the dose of 30 mg/Kg (175 mole/Kg) did not produce a significant antiallodynic effect (Table 4). At the dose of 100 mg/kg (584 μmole/Kg), induced motor impairment and sedation (Table 5), which made it difficult to evaluate its anti-allodynic effect.

EXAMPLE F 5

In this experiment the effect of repeated administration of NO-gabapentin was assessed and compared with that of the precursor drug gabapentin in a rat model of neuropathic pain. In 4 groups of female Sprague-Dawley rats weighting 200 g photochemically-induced ischemic spinal cord injury was produced according to methods describe by Xu et al. Pain, 1992, 48, 279–290.

Spinally-injured rats developed a chronic pain syndrome, including marked mechanical and cold allodynia. The rats were injured 3–6 months before the beginning of the experiment. Each of the groups of rats were i.p. treated daily for 10 day, respectively, with 60 mg/kg (167,2 μmole/Kg) of NO-gabapentin and with 30 mg/Kg (175 μmole/Kg) of gabapentin. Controls (two groups) received only the vehicle. Each day the treatment of the animals was made at the same time. During the experiment vocalized thresholds to graded mechanical touch/pressure were tested with von Frey hairs.

During testing, rats were gently restrained in a standing position and the von Frey hair was pushed onto the skin until filament becomes bent. The frequency of stimulation was about 1/s and repeated 5–10 times. The intensity of stimulation (g) which induced consistent vocalization (>75% response rate) is considered as pain threshold. Behavioral testings were carried out before the daily for the control group and 1 hour after administration for the treated groups.

The effect of chronic daily administration of gabapentin and NO-gabapentin is reported in Table 6. NO-gabapentin alleviated mechanical allodynia following the first administration and a significant effect was maintained up to day 6. Gabapentin did not produce a significant effect up to the second day and the effect was lower than that of NO-gabapentin.

TABLE 1

Evaluation of the analgesic activity of gabapentin and of the NO-gabapentin derivative in the experiment F1 (rats injected in a paw with formalin)

| Treatment | Dose (mg/kg) | Number "paw licking" % |
|---|---|---|
| Controls | | 100 |
| Gabapentin | 90 | 80 |
| NO-Gabapentin | 50 | 70 |

TABLE 2

Ex. F2: analgesic activity of the drugs used in the chronic (neuropathic) pain treatment in combination with a nitric oxide-donor drug

| Treatment | response % |
|---|---|
| Controls | 100 |
| Clomipramine | 72 |
| NO-ASA | 82 |
| Clomipramine + NO-ASA | 29 |

TABLE 3

Rex. F3: acute toxicity of gabapentin and NO-gabapentin in diabetic rats

| Treatment | lethality % |
|---|---|
| Controls | 10 |
| Gabapentin | 50 |
| NO-gabapentin | 20 |

TABLE 4

Ex. F4: effect of different doses of NO-gabapentin and gabapentin on cold stimulation in a rat model of neuropathic pain. Response is evaluated with by a score (0–3).

| Compound | Dose (μmole/kg) | Time (min) 0 | 30 | 120 | 240 |
|---|---|---|---|---|---|
| Control | — | 2 | 2 | 2 | 2 |
| NO-gabapentin | 55.7 | 2 | 2 | 2 | — |
| NO-gabapentin | 167.2 | 2 | 1 | 1 | — |
| NO-gabapentin | 278.7 | 2 | 1 | 1 | 1 |
| Gabapentin | 175 | 2 | 2 | 2 | 2 |
| gabapentin | 584 | — | — | — | — |

TABLE 5

Ex. F4: effect of different acute doses of NO-gabapentin and gabapentin on motor performance in a rat model of neuropathic pain.

| Compound | Dose kg) | Time (μmole/(min) 0 | 30 | 120 | 240 |
|---|---|---|---|---|---|
| Control | — | 15 | 15 | 15 | 15 |
| NO-gabapentin | 55.7 | 14 | 14 | 14 | — |
| NO-gabapentin | 167.2 | 14 | 14 | 15 | — |
| NO-gabapentin | 278.7 | 14 | 15 | 14 | 14 |
| Gabapentin | 175 | 20 | 20 | 20 | 20 |
| Gabapentin | 584 | 15 | 30 | 30 | 25 |

TABLE 6

Ex. F5: effect of repeated administration of NO-gabapentin and gabapentin on vocalization threshold (g) to mechanical stimulation with von Frey hairs in a rat model of neuropathic pain.

| Compound | Dose (μmole/kg) | Day 1 | 2 | 4 | 6 |
|---|---|---|---|---|---|
| Baseline | — | 2 | 5 | 8 | 2 |
| NO-gabapentin | 167.2 | 100 | 200 | 400 | 90 |
| Baseline | — | 5 | 3 | 3 | 5 |
| Gabapentin | 175 | 5 | 6 | 70 | 90 |

The invention claimed is:

1. Nitrooxyderivative compounds or salts thereof having the following general formula (I):

wherein:

c0 is 1;

b0 is an integer and is 0 or 1;

A=R—T$_1$—, wherein R is the radical of an analgesic drug having formula II:

wherein:

W is a carbon atom;

m is an integer from 0 to 2;

$R_0$=H, —(CH2)$_n$—NHR$_{1A}$, n being an integer equal to 0 or 1, wherein R$_{1A}$=H;

$R_1$=H;

$R_2$ is chosen between the following groups:

3-4 di-hydroxy substituted benzyl;

the radical of formula (IIA), wherein optionally one unsaturation of ethylene type can be present between the carbon atoms in position 1 and 2:

$$Q-\text{}^5(CH)_{p_3}-\text{}^4(CH)_{p_2}-\text{}^3(C)_{p_1}-\text{}^2CH-\text{}^1CH- \quad (IIA)$$
$$\underset{(R_{6A})_p}{|}$$
(with substituents $R_8, R_7, R_6, R_5, R_4$)

wherein:
p and $p_1$ are integers, equal to or different from each other and are 0 or 1;
$p_2$ and $p_3$ are equal to 0;
$R_4$ is hydrogen;
$R_5$ is hydrogen or —$CH_3$;
$R_6$ and $R_{6A}$ are H;
$R_7$ and $R_8$ equal to or different, are H, methyl; or free valence;
with the proviso that in the radical of formula (IIA) when one unsaturation of ethylene type between $C_1$ and $C_2$ is present, $R_4$ and $R_5$ are free valences such as to form the double bond between $C_1$ and $C_2$; when the unsaturation is between $C_4$ and $C_5$, $R_7$ and $R_8$ are free valences such as to form the double bond between $C_4$ and $C_5$;
Q is equal to H, —$OH_3$, guanidine ($H_2NC(=NH)NH—$), or thioguanidine ($H_2NC(=S)NH—$); wherein in formula (II), $R_2$ with $R_1$ and with W=C taken together form a $C_6$ saturated ring;
$T_1=(CO)_t$ or $(X)_{t'}$, wherein X=O, S, $NR_{1C}$, $R_{1C}$ is H or a linear or branched alkyl, having from 1 to 5 carbon atoms, t and t' are integers and equal to zero or 1, with the proviso that t=1 when t'=0; t=0 when t'=1
B=—$T_B$—$X_2$—$T_{BI}$—wherein
$T_B$ and $T_{BI}$ are equal or different;
$T_B=(GO)$ when t=0, $T_8$=X when t'=0, X being as above;
$T_{BI}=(CO)_{tx}$ or $(X)_{txx}$, wherein tx and txx have the value of 0 or 1;
with the proviso that tx=1 when txx=0; and tx=0 when txx=1; X is as above;
$X_2$, bivalent radical, is such that the corresponding precursor of B $T_B$-$X_2$-$T_{BI}$-wherein the free valences of $T_6$ and of $T_{BI}$ are saturated each with OZ, with Z or with —N(Z')(Z''), being:
Z=H, $C_1$–$C_{10}$, preferably $C_1$–$C_5$ alkyl linear or branched when possible,
Z', Z'' equal to or different have the values of Z as above, depending on that $T_B$ and/or
$T_{BI}$=CO or X, in function of the values of t, t', tx and txx; the precursor compound of B as above defined being selected from the following classes of compounds:
aminoacids, selected from the following: L-carnosine, anserine, selenocysteine, selenomethionine, penicillamine, N-acetylpenicillamine, cysteine, N-acetylcysteine, glutathione or esters thereof, preferably ethyl or isopropyl ester;
hydroxyacids, selected from the following: gallic acid, ferulic acid, gentisic acid citric acid, caffeic, dihydrocaffeic acid, p-cumaric acid, vanillic acid;
C=bivalent radical —$T_C$—Y—wherein
when b0=c0=1: $T_C$=(CO) when tx=0, $T_C$=X when txx=0, X being as above defined;
when b0=0: $T_C$=(CO) when t=0, $T_C$=X when t'=0, X being as above defined;
when c0=0: tx=0, $T_{BI}$=X=—O—;
Y has one of the following meanings;

$Y_0$, selected from the following: R'O wherein R'is a linear or branched when possible $C_1$–$C_{20}$alkyl
or Y is selected from one of the following groups:

$$—(CH_2—\underset{\underset{ONO_2}{|}}{CH}—CH_2—O)\overline{_{nf'}};$$

$$(CH_2—\underset{\underset{ONO_2}{|}}{CH}—CH_2—O)\overline{_{nf'}}—$$

wherein nf' is an integer from 1 to 6;

$$—(\underset{\underset{R_{1f}}{|}}{CH}—CH_2—O)_{nf}—; \quad —(CH_2—\underset{\underset{R_{1f}}{|}}{CH}—O)_{nf}—$$

wherein $R_{1f}$=H, $CH_3$ and nf is an integer from 1 to 6;
$Y_{AR}$, selected from:
$Y_{AR1}$:

(V) phenyl ring with —$(CH_2)_{n3}$— and —$(CH_2)_{n3'}$—O substituents wherein n3 is an integer from 0 to 5 and n3'is an integer from 1 to 3; or
$Y_{AR2}$:

(VI) ring with —$(CH_2)_{n3'}$—O and HOOC—$(CH_2)_{n3}$— substituents wherein n3 and n3' have the above meaning.

2. Compounds according to claim 1, wherein:
when in formula (II) W=C, m=1 and $R_0$=—$(CH_2)_n$—$NH_2$ with n=1, $R_2$ and $R_1$ with W as above defined form together the cyclohexane ring, in the radical A of formula (I) $T_1$=CO and the free valence of A is saturated with OH, the precursor drug of R is known as gabapentin;
when in formula (II) W=C, m=0 and $R_0$=—$(CH_2)_n$—$NH_2$ with n=0, $R_1$=H, $R_2$ is the radical of formula (IIA) wherein p=$p_1$=1, $p_2$=$p_3$=0, $R_4$=$R_5$=$R_6$=$R_{6A}$=H, Q =H, in the radical A of formula (I) $T_1$=CO and the free valence of A is saturated with OH, the precursor drug of R is known as norvaline;
when in formula (II) W=C, m=0 and $R_0$=—$(CH_2)_n$—$NH_2$ with n=0, $R_1$=H, $R_2$ is the radical of formula (IIA) wherein p=$p_1$=1, $p_2$=$p_3$0, $R_4$=$R_5$=$R_6$=$R_{6A}$=H, Q is the guanidine group, in the radical A of formula (I) $T_1$=CO and the free valence of A is saturated with OH, the precursor drug of R is known as arginine;

when in formula (II) W=C, m=0 and $R_0$=—$(CH_2)_n$—$NH_2$ with n =0, $R_1$=H, $R_2$ is the radical of formula (IIA) wherein p=$p_1$=1, $p_2$=$p_3$=0, $R_4$=$R_5$=$R_6$=$R_{6A}$=H, Q is the thioguanidine group, in the radical A of formula (I) $T_1$=CO and the free valence of A is saturated with OH, the precursor drug of R is known as thiocitrulline;

when in formula (II) W=C, m=1 and $R_0$=—$(CH_2)_n$—$NH_2$ with n=1, $R_1$=H, $R_2$ is the radical of formula (IIA) wherein p=$p_1$=$p_2$=$p_3$=0, $R_4$=H, $R_5$=Q $CH_3$, in the radical A of formula (I) $T_1$=CO and the free valence of A is saturated with OH, the precursor drug of R is known as pregabalin;

when in formula (II) W=C, and has configuration (S), m=1 and $R_0$=—$(CH_2)_n$—$_{NH2}$ with n=1, $R_1$=H, $R_2$ is the radical of formula (IIA) wherein p=$p_1$=$p_2$=$p_3$=0, $R_4$=H, $R_5$=Q=$CH_3$, in the radical A of formula (I) $T_1$=CO and the free valence of A is saturated with OH, the precursor drug of R is known as (S) 3-isobutylGABA;

when in formula (II) W=C, m=1 and $R_0$=$R_1$=H, $R_2$ is the radical of formula (IIA) wherein p=$p_1$=1, $p_2$=$p_3$=0, $R_4$=$R_5$=$R_6$=$R_{6A}$=H, Q is the guanidine group, in the radical A of formula (I) $T_1$=NH and the free valence of A is saturated with H, the precursor drug of R is known as agmatine;

when in formula (II) W=C, m=2 and $R_0$=—$(CH_2)_n$—$NH_2$ with n=0, $R_1$=H, $R_2$ is the radical of formula (IIA) wherein p=$p_1$=$p_2$=$p_3$=0, $R_4$ and $R_5$ are free valences and between $C_1$ and $C_2$ there is one ethylene unsaturation, Q=H, in the radical A of formula (I) $T_1$=CO and the free valence of A is saturated with OH, the precursor drug of R is known as vigabatrin;

when in formula (II) W=C, m=0 and $R_0$=—$(CH_2)_n$—$NH_2$ with n=0, $R_1$=H, $R_2$ is the radical 3-4 di-hydroxy substituted benzyl, $T_1$=CO and the free valence of A is saturated with OH, the precursor drug of R is known as 2-amino-3-(3,4-dihydroxyphenyl)propanoic acid (dopa).

3. Compounds according to claim 1, wherein when in formula (I) b0=0, Y in the bivalent linking group C is $Y_{AR}$ as above defined.

4. Compounds according to claim 1, wherein in formula (I) the precursors of B are the following: ferulic acid, N-acetylcysteine, cysteine, caffeic acid, hydro-caffeic and gentisic acid.

5. Compounds according to claim 1, selected from the following:

1-(aminomethyl)cyclohexan acetic acid 2-methoxy-4-[(1E)-3[4-(nitrooxy) butyoxy]-3-oxy-1-propoxy]phenyl hydrochloride ester (XV)

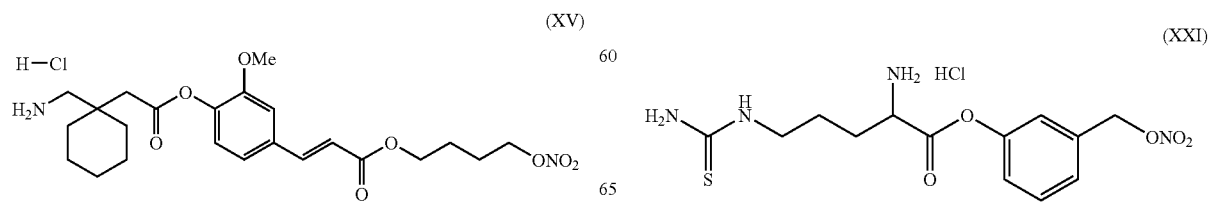

1-(aminomethyl)cyclohexan acetic acid 3-(nitrooxymethyt) phenyl hydrochloride ester (XVI)

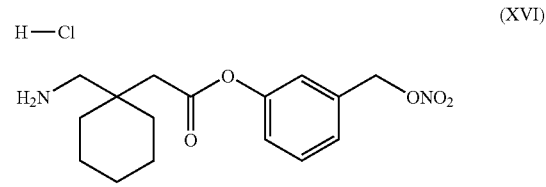

2-aminopentanoic acid 3-(nitrooxymethyl) phenyl hydrochloride ester (XVII)

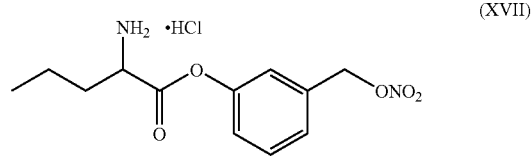

(S)-N-acetylcysteine-, 4-(nitrooxy)butyl ester, 2-amino hydrochloride pentanoate (XVIII)

(S)-N-acetylcysteine-, 4-(nitrooxy)butyl ester, 1-(aminomethyl) cyclohexanacetate hydrochloride (XIX)

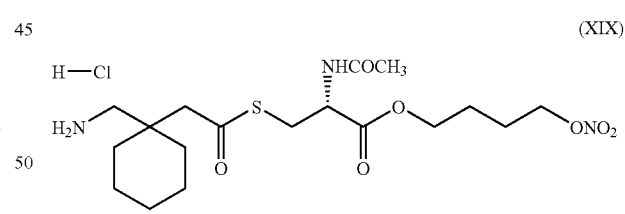

alpha-amino-delta-thioureidopentanoic acid, 3-(nitrooxy methyl)phenyl hydrochloride ester (XXI)

(S)-N-acetylcysteine-, 4-(nitrooxy)butyl ester, alpha-amino, delta-thioureidopentanoate hydrochloride (XXII)

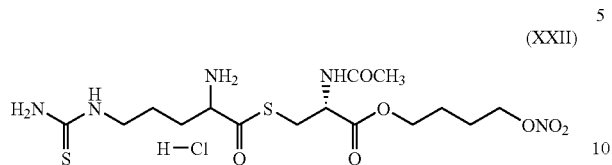

(XXII)

alpha-amino-delta-thioureidopentanoic acid, 2-me-thoxy-4-[(1E)-3-[4-(nitrooxy)butoxy]-3-oxy-1-propenyl]phenyl hydrochloride ester (XXIII)

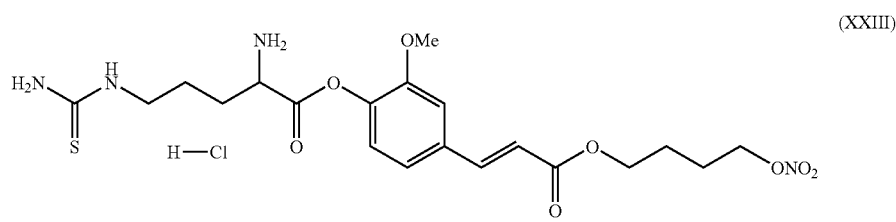

(XXIII)

2-amino-5-guanidinopentanoic acid, 3-(nitrooxy methyl) phenyl hydrochloride ester (XXIV)

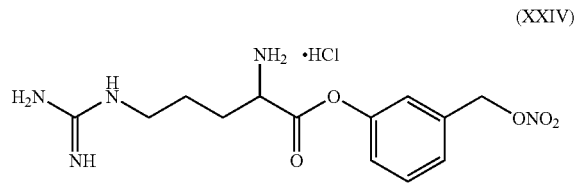

(XXIV)

2-amino-5-guanidinopentanoic acid-, 2-methoxy-4-[(1E)-3-[4-(nitrooxy)butoxy]-3-oxy-1-propenyl]phenyl hydrochloride ester (XXV)

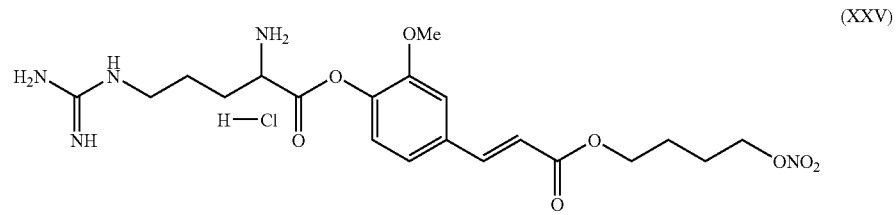

(XXV)

(S)-N-acetylcysteine-4-(nitrooxy)butyl ester, 2-amino-5-guanidinopentanoate hydrochloride (XXVI)

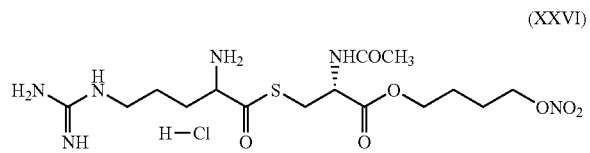

(XXVI)

4-(guanidine)butyl-3-nitrooxymethylbenzamide (XXVII)

(XXVII)

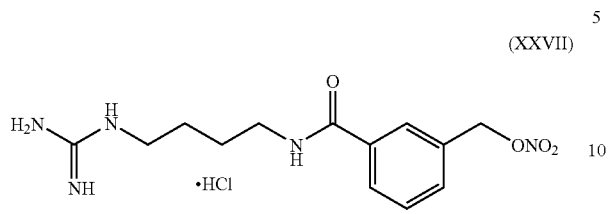

4-(guanidine)butyl-3-[4-(4'-nitrooxybutyryloxy)-3-(methoxy)]phenyl-2-propenamide chloride (XXVIII)

(XXVIII)

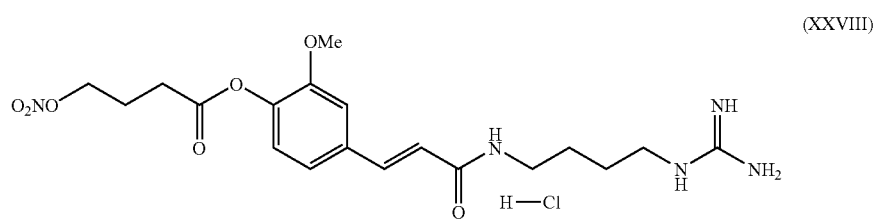

1-(aminomethyl)cyclohexan acetic acid 4-(nitroxy)butyl hydrochloride ester (XXIX)

(XXIX)

6. Compounds according to claim 1, as nitrate salts.

7. Pharmaceutical compositions for parenteral, oral and topical use, comprising the compounds according to claim 1.

8. A method of treating chronic pain, comprising administering to a subject a compound according to claim 1.

9. The method of claim 8, wherein the chronic pain is neuropathic pain.

\* \* \* \* \*